United States Patent [19]

Opitz et al.

[11] Patent Number: 4,539,402
[45] Date of Patent: Sep. 3, 1985

[54] QUINAZOLINONE DERIVATIVES

[75] Inventors: Wolfgang Opitz, Overath; Haireddin Jacobi, Leichlingen; Bernhard Pelster, St. Augustin, all of Fed. Rep. of Germany

[73] Assignee: Troponwerke GmbH & Co., Cologne, Fed. Rep. of Germany

[21] Appl. No.: 492,775

[22] Filed: May 9, 1983

[30] Foreign Application Priority Data

May 29, 1982 [DE] Fed. Rep. of Germany ....... 3220438

[51] Int. Cl.$^3$ ............................................ C07D 287/04
[52] U.S. Cl. .................................... 544/247; 544/250; 544/315; 548/329; 548/351
[58] Field of Search ................. 544/247, 250; 424/251

[56] References Cited

U.S. PATENT DOCUMENTS

| | | |
|---|---|---|
| 3,669,969 | 6/1972 | Lunn .................................... 544/247 |
| 3,905,976 | 9/1975 | Hardtmann ......................... 544/250 |
| 3,963,720 | 6/1976 | Hardtmann ......................... 544/247 |
| 3,984,556 | 10/1976 | Hardtmann ......................... 544/250 |

OTHER PUBLICATIONS

Lunn, et al., "J. Het. Chem.", vol. VIII, 1971, pp. 141-147.

*Primary Examiner*—Glennon H. Hollrah
*Assistant Examiner*—James H. Turnipseed
*Attorney, Agent, or Firm*—Sprung, Horn, Kramer & Woods

[57] ABSTRACT

The invention relates to quinazolinone derivatives and of formula (I) as defined herein and processes for the production of said derivatives. Also included in the invention are pharmaceutical compositions containing a compound of said formula (I) as active ingredient and the use of said compounds and compositions as anti-inflammatory agents.

5 Claims, No Drawings

QUINAZOLINONE DERIVATIVES

The present invention relates to new quinazolinone derivatives, a process for their preparation and their use as pharmaceuticals.

German Offenlegungsschriften Nos. 2,234,174 and 2,257,376 and U.S. Pat. Nos. 3,887,559, 3,905,976, 3,969,506, 3,982,000 and 3,984,556 describe bronchodilatory and hypotensive actions and actions on the central nervous system for somewhat related compounds. Surprisingly, it has now been found that the new quinazolinone derivatives have interesting anti-inflammatory actions. As claimed, without measurement results being given, for the compounds contained in the applications mentioned, individual compounds have an action on the central nervous system; they are distinguished by powerful analgesic and sedating actions.

The present invention reates to new quinazolinone derivatives of the general formula I

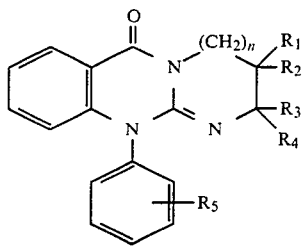

in which
(a) $R_1$, $R_2$, $R_3$ and $R_4$ each represent hydrogen and n represents 0 or 1, or
(b) $R_1$ and $R_3$ represent hydrogen, $R_2$ and $R_4$ together represent a bond and n represents 0, or
(c) $R_1$ and $R_3$ together represent a bond, $R_2$ and $R_4$ represent the grouping

and n represents 0,
and in which, in each case,
$R_5$ represents a halogenated alkyl group; an alkylthio group or a group resulting therefrom by oxidation; a nitro group or an optionally substituted amino group, and their physiologically acceptable salts with acids.

The halogenated alkyl group defining $R_5$ is preferably a lower alkyl radical with 1 to 4C atoms, which is completely or partly substituted by halogen atoms, preferably by chlorine or fluorine atoms such as difluoromethyl, trifluoromethyl, trichloromethyl or pentafluoroethyl especially preferred halogenated alkyl groups are those containing 1 or 2 carbon toms and 2 to 5 halogen atoms.

Preferred alkylthio groups are those with lower alkylthio radicals with 1 to 3C atoms; by the oxidation products which can be prepared therefrom there are to be understood those compounds of the general formula I in which $R_5$ represents an alkylsulphinyl or alkylsulphonyl group; optionally substituted amino groups are free amino groups and amino groups which are substituted by 1 or 2 lower alkyl radicals with up to 3C atoms or by one acyl (especially carboxylic acid acyl) radical containing up to 3C atoms, such as a $C_1$–$C_3$-alkanoyl group. radical containing up to 3C atoms.

Compounds of the formula I in which
$R_1$, $R_2$, $R_3$ and $R_4$ each represent a hydrogen atom and n represents 0 or 1, or
$R_1$ and $R_3$ represent hydrogen atoms,
$R_2$ and $R_4$ together represent a bond and n represents 0, or
$R_1$ and $R_3$ together represent a bond, $R_2$ and $R_4$ together represent the grouping

and n represents 0,
and in which
$R_5$ represents a trifluoromethyl, methylthio, methylsulphonyl, nitro or amino group,
are of particular interest.

Compounds of the formula I, according to the invention, in which $R_1$, $R_2$, $R_3$ and $R_4$ each represent hydrogen and n represents 0 or 1 or $R_1$ and $R_3$ together represent a bond, $R_2$ and $R_4$ together represent the grouping

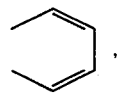, n represents 0 and $R_5$ represents a halogenated alkyl, alkylthio or nitro group are obtained by a process in which the corresponding N-arylanthranilic acid II is converted into an activated carboxylic acid derivative III with suitable activation reagents (a survey can be found in, for example, Houben-Weyl "Methoden der Organischen Chemie", ("Methods of Organic Chemistry"), volume 15/2, Georg Thieme Verlag Stuttgart, 1974).

According to the invention, the reaction of II with $PCl_5$ provides III in which X is chlorine;

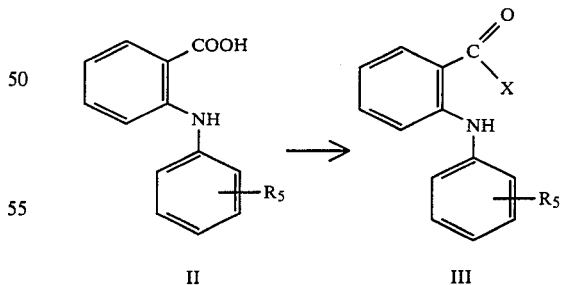

compare J. Amer. Chem. Soc. 68, 2112 (1946)) or with dicyclohexylcarbodiimide and pentachlorophenol which provides III in which X is $OC_6Cl_5$; compare Helv. Chim. Acta 46, 1609 (1963) is preferred.

The anthranilic acid derivatives III thus obtained can be reacted, either as pure isolated compounds or without prior isolation in suitable aprotic solvents, such as, for example, dimethylformamide, dioxane or tetrahydrofuran or mixtures of these solvents, preferably dioxane, with S-alkylated, preferably methylated, cyclic isothiourea derivatives IV

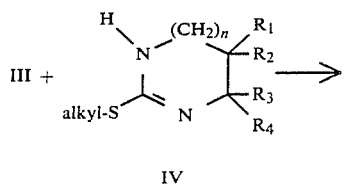

III +

IV

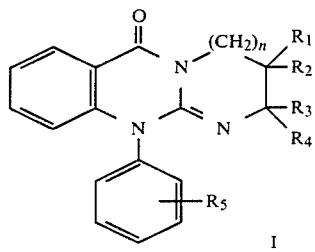

I in which
R₁, R₂, R₃ and R₄ each represent hydrogen and n represents 0 or 1, or
R₁ and R₃ together represent a bond,
R₂ and R₄ together represent the grouping

and n represents 0,
which isothiourea derivatives are known from the literature, to give the corresponding compounds of the formula I according to the invention with R₅ defined as above.

The reaction (III+IV→I) is carried out at elevated temperature, preferably at a temperature of about 40° C. below the boiling point of the solvent up to and including the boiling point of the solutions used. The reaction is very particularly preferably carried out at the boiling point of the solution used. Although it is also possible to carry out the reaction at even lower temperatures, a longer time then being required.

From a resulting compound of the formula I in which R₅ represents alkylthio, another compound of the formula I, according to the invention, in which R₅ represents alkylsulphinyl or alkylsulphonyl can be prepared with a suitably oxidizing agent, preferably hydrogen peroxide or percarboxylic acids, such as peracetic, perbenzoic etc. said in a suitable solvent of—e.g. a glacial acetic acid.

The reaction of a compound of the formula I, according to the invention, in which R₁, R₂, R₃ and R₄ each represents a hydrogen atom and n represents 0, with oxidizing agent, such as, for example, active manganese dioxide (compare J. Org. Chem. 33, 3758 (1968)) gives compounds of the formula I, according to the invention, in which R₁ and R₃ represents a hydrogen atom, R₂ and R₄ together represent a bond and n represents 0.

The reduction, for example by catalytic hydrogenation, of the compounds of the formula I, according to the invention, in which R₅ represents nitro gives compounds of the formula I, according to the invention, in which R₅ represents amino.

Surprisingly, the compounds of the formula I according to the invention exhibit very powerful anti-inflammatory, analgesic and sedating actions coupled with a comparatively low toxicity, and they thus represent an enrichment of pharmacy.

Specific examples which may be mentioned of the compounds of the formula I according to the invention are: 10-(3-methylthiophenyl)-2,3-dihydroimidazo[2,2-b]-quinazolin-5(10H)-one, 10-(4-methylthiophenyl)-2,3-dihydroimidazo[2,1-b]-quinazolin-5(10H)-one, 10-(3-nitrophenyl)-2,3-dihydroimidazo[2,1-b]-quinazolin-5(10H)-one, 10(-3-trifluoromethyl)-2,3-dihydroimidazo[2,1-b]-quinazolin-5(10H)-one, 10-(3-aminophenyl)-2,3-dihydroimidazo-[2,1-b]-quinazolin-5(10H)-one, 10-(4-methylsulphinylphenyl)-2,3-dihydroimidazo-[2,1-b]-quinazolin-5(10H)-one, 10-(3-trifluoromethylphenyl)-imidazo[2,1-b]-quinazolin-5(10H)-one, 5-(3-nitrophenyl)-benzimidazo[2,1-b]-quinazolin-12(5H)-one and 11-(3-nitrophenyl)-2,3,4,6-tetrahydropyrimido[2,1-b]-quinazolin-6-one.

The antiphlogistic action can be demonstrated by the method of Winter et al., Proc. Soc. Exp. Biol. Med. 111, 544 (1962), with the modification that pure λ-carrageenan as a 0.25% strength suspension in physiological saline solution was used for oedema provocation. The following ED₅₀ values, for example, were determined using this procedure:

| Compound from example | ED₅₀ carrageenan oedema peroral |
| --- | --- |
| 4 | 1.3 mg/kg |
| 5 | 25.2 mg/kg |
| 9 | 3.1 mg/kg |

Influence on orientation motility in mice was tested to determine the sedative action; an ED₅₀ of 0.5 mg/kg perorally was found for the compound of Example 4. The ED₅₀ of diazepam in the same test is 2.8 mg/kg perorally, and that of chlorpromazine is 3.05 mg/kg perorally.

The analgesic action of the compound of Example 4 was determined in the Randall-Selitto test (ED₅₀ 3.4 mg/kg perorally, rats) and in the benzoquinone test (ED₅₀ 3.1 mg/kg perorally; mice).

The resulting active compounds can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxy-ethanesulfonic, ethylenesulfonic, benzenesulfonic, halogenobenzenesulfonic, toluensulfonic, naphthalenesulfonic and sulfanilic acid; methionine, tryptophan, lysine and arginine. Salts of the above-mentioned acids or other salts, for example, the pricrates, can also be used for purification of the bases obtained; the bases are converted into salts, the salts are separated and the bases are liberated from the salts. In view of the close relationship between the free compounds and the compounds in the form of their salts, whenever a compound is referred to this context, a corresponding salt is also intended, provided such is possible or appropriate under the circumstances.

The present invention includes pharmaceutical formulations which, in addition to non-toxic, inert, pharmaceutically suitable excipients, contain one or more active compounds according to the invention, or which consist of one or more active compounds according to the invention, as well as processes for the preparation of these formulations.

The present invention also includes pharmaceutical formulations in dosage units. This means that the formulations are in the form of individual parts, for example tablets, dragees, capsules, pills, suppositories and ampoules, of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions, pastes, ointments, gels, creams, lotions, powders and sprays are preferred pharmaceutical formulations.

Tablets, dragees, capsules, pills and granules can contain the active compound or compounds alongside the customary excipients, such as fillers and extenders (for example starches, lactose, sucrose, glucose, mannitol and silica), binders (for example carboxymethylcellulose, alginates, gelatines and polyvinylpyrrolidone), humectants (for example glycerol), distintegrating agents (for example agar-agar, calcium carbonate and sodium bicarbonate), solution retarders (for example paraffin) and resorption accelerators (for example quaternary ammonium compounds), adsorbents (for example kaolin and bentonite) and lubricants (for example talc, calcium stearate and magnesium stearate and solid polyethylene glycols) or mixtures of the substances mentioned.

The tablets, dragees, capsules, pills and granules can be provided with the customary coatings and shells, optionally containing opacifying agents, and can also be of such composition that they release the active compound(s) only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a microencapsulated form, to achieve a retarded effect.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound or compounds, the customary excipients (for example animal and vegetable fats, waxes, paraffins, starches and tragacanth) or mixtures of these substances.

Powders and sprays can contain, in addition to the active compound or compounds, the customary excipients (for example lactose, talc, silica and aluminium hydroxide), or mixtures of these substances. Sprays can additionally contain the customary propellants.

Solutions and emulsions can contain, in addition to the active compound or compounds, the customary excipients, such as solvents, solubilising agents and emulsifiers, for example water, ethyl alcohol, isopropyl alcohol, ethyl carbonate, ethyl acetate, benzyl alcohol, benzyl benzoate, propylene glycol, oils, especially cottonseed oil, groundnut oil, maize germ oil, olive oil and sesame oil, glycerol and polyethylene glycols, or mixtures of these substances.

For parenteral administration, the solutions and emulsions can also be in a sterile form which is isotonic with blood.

Suspensions can contain, in addition to the active compound or compounds, the customary excipients, such as liquid diluents (for example water, ethyl alcohol and propylene glycol), suspending agents (for example ethoxylated isostearyl alcohols, polyoxyethylene sorbitol esters and sorbitan esters and microcrystalline cellulose), or mixtures of these substances.

The formulation forms mentioned can also contain colorants, preservatives and additives which improve the odour and flavour, for example peppermint oil and eucalyptus oil, and sweeteners, for example saccharin.

The therapeutically active compounds are preferably present in the abovementioned pharmaceutical formulations in a concentration of about 0.1 to 99.5% by weight, preferably about 0.5 to 95% by weight, of the total mixture.

The abovementioned pharmaceutical formulations can also contain other pharmaceutical active compounds in addition to the active compounds according to the invention.

The abovementioned pharmaceutical formulations are prepared in the customary manner according to known methods, for example by mixing the active compound or compounds with the excipient or excipients.

The present invention also includes the use of the active compounds according to the invention, and of pharmaceutical formulations which contain one or more active compounds according to the invention, in medicine, for the treatment of inflammatory processes in warm-blooded animals.

The active compounds or the pharmaceutical formulations can be administered topically, orally, parenterally, intraperitoneally and/or rectally, preferably orally or cutaneously.

In general, it is to be regarded as advantageous in medicine to administer the active compound or compounds according to the invention in total amounts of about 0.1 to 200 mg, preferably 0.1 to 70 mg, per 24 hours, per ma al optionally in the form of several individual administrations, in order to achieve the desired results.

However, it can be necessary to deviate from the dosages mentioned, and in particular to do so as a function of the nature and body weight of the subject to be treated, the nature and severity of the disease, the nature of the formulation and of the administration of the medicament and the period or interval over which the administration takes place. Thus it can in some cases suffice to manage with less than the abovementioned amount of active compound, whilst in other cases the abovementioned amount of active compound must be exceeded.

The particular optimum dosage required and the type of administration of the active compounds can easily be determined by anyone skilled in the art on the basis of his expert knowledge.

The present invention is illustrated in more detail by the examples which follow, but of course, is not limited thereto.

EXAMPLES 1. 2-(3-Trifluoromethylphenylamino)-benzoyl chloride

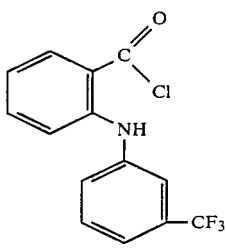

78.5 g (0.376 mol) of PCl$_5$ are added in portions to a suspension of 100 g (0.356 mol) of 2-(3-trifluoromethylphenylamino)-benzoic acid in 175 ml of toluene at 5°–10° C., whilst stirring and flushing with nitrogen, and the mixture is subsequently stirred for 30 minutes, whilst cooling. The reaction solution is washed, with vigorous thorough stirring, with five 50 ml portions of water, under nitrogen and whilst cooling with ice, and is dried over Na$_2$SO$_4$ and evaporated in vacuo at 40°, and petroleum ether is added to the oily evaporation residue. The chloride crystallises out in the cold. Yield: 90.4 g (85% of theory) melting point 63°–65° C.

2. The following compound is obtained using the same procedure as that used for procurement of 2-(3-trifluoromethylphenylamino)-benzoyl chloride except that an equivalent amount of 2-(3-nitrophenylamino)-benzoic acid is used in place of the 2-(3-trifluoromethylphenylamino)-benzoic acid of the reference example from 2-(3-nitrophenylamino)-benzoic acid: 2-(3-Nitrophenylamino)-benzoyl chloride

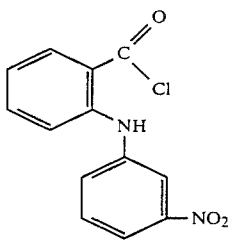

Yield: 77% of theory, melting point: 141°–145° C.

3. 10-(4-Methylthiophenyl)-2,3-dihydroimidazo-[2,1-b]-quinazolin-5(10H)-one

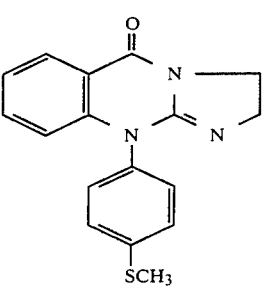

7.8 g (30 mmols) of 2-(4-methylthiophenylamino)-benzoic acid are suspended in 150 ml of n-hexane, 7.1 g (34 mmols) of PCl$_5$ are added and the mixture is stirred at room temperature for 2 hours and is then stored overnight. The mixture is filtered, the precipitate is dissolved in 120 ml of dioxane, 3.8 g (33 mmols) of 2-methylthioimidazoline are added, the mixture is boiled under reflux for 90 minutes and the solvent is evaporated off in vacuo. Water is added to the residue and the mixture is acidified with 2N HCl and filtered. The solution is adjusted to pH 9–10 with 2N NaOH and extracted with methylene chloride. After the organic phase has been dried and evaporated, the residue is crystallised from methylene chloride and petroleum ether. Yield: 4.5 g (48.5% of theory), melting point 226°–227° C.; N calculated 13.58%; N found 13.45%.

4. 10-(3-Nitrophenyl)-2,3-dihydroimidazo-[2,1-b]-quinazolin-5(10H)-one

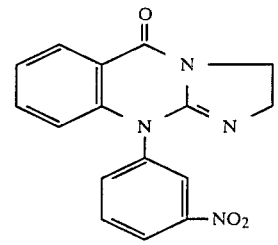

A suspension of 11 g (40 mmols) of 2-(3-nitrophenylamino)-benzoyl chloride and 5.1 g (44 mmols) of 2-methylthioimidazoline in 160 ml of dioxane is boiled under reflux for 1 hour, the solvent is evaporated off in vacuo and the residue is partitioned between methylene chloride and saturated KHCO$_3$ solution. The organic phase is dried over Na$_2$SO$_4$ and evaporated and the residue is crystallised from methylene chloride by the addition of diisopropyl ether. Yield: 5.8 g (47% of theory), melting point 275°–277° C.; N calculated 18.17%; N found 18.47%.

5. 10-(3-Trifluoromethylphenyl)-2,3-dihydroimidazo-[2,1-b]-quinazolin-5(10H)-one

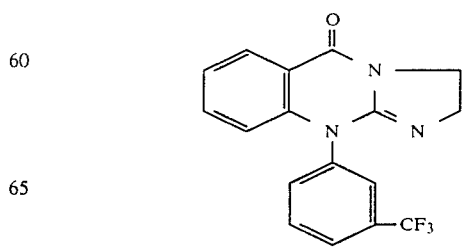

2.8 ml (20 mmols) of triethylamine in 10 ml of dioxane are added to a suspension of 6 g (20 mmols) of 2-(3-trifluoromethylphenylamino)-benzoyl chloride and 4.9 g (20 mmols) of 2-methylthioimidazole hydriodide in 50 ml of dioxane at room temperature, and the mixture is boiled under reflux for 2 hours. The solvent is stripped off, the residue is partitioned between methylene chloride and aqueous NaOH (pH 9–10), the organic phase is dried over Na₂SO₄ and evaporated and the residue which remains is crystallised from methylene chloride/diisopropyl ether. Yield: 3.65 g (55% of theory), melting point 251°–252° C.; N calculated 12.68%; N found 12.72%.

6. Analogously, the following compound was prepared from 2-(3-nitrophenylamino)-benzoyl chloride and 2-methyl-thioΔ²-tetrahydropyrimidine hydriodide (J. Amer. Chem. Soc. 78, 1618 (1956)): 11-(3-nitrophenyl-2,3,4,6-tetrahydropyrimido[2,1-b]-quinazolin-6-one

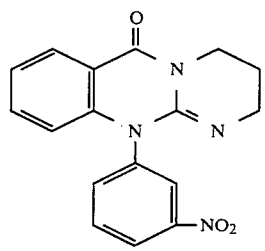

Yield: 43% of theory, melting point 249°–250° C.; N calculated 17.36%; N found 17.51% and 7. the following compound was prepared from 2-(3-nitrophenylamino)-benzoyl chloride and 2-methylthiobenzimidazole: 5-(3-nitrophenyl)-benzimidazo-[2,1-b]-quinazolin-12(5H)-one

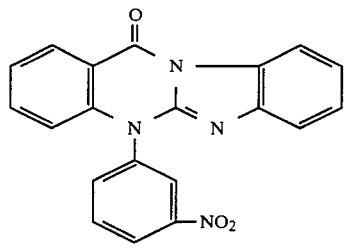

Yield: 62% of theory, melting point 294° C.; N calculated 15.72%; N found 15.73%.

8. 10-(3-Methylthiophenyl)-2,3-dihydroimidazo-[2,1-b]-quinazolin-5(10H)-one

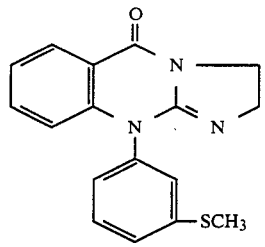

A solution of 16.3 g (63 mmols) of 2-(3-methylthiophenylamino)-benzoic acid and 16.8 g (63 mmols) of pentachlorophenol in 80 ml of dimethylformamide is combined with a second solution of 13 g (63 mmols) of dicyclohexylcarbodiimide in 20 ml of dimethylformamide, and the reaction mixture is stored at room temperature for 2 hours. The dicyclohexylurea which has precipitated is filtered off and a mixture of 15.4 g (63 mmols) of 2-methylthioimidazoline hydriodide and 8.7 ml (63 mmols) of triethylamine in 40 ml of dimethylformamide is added to the filtrate. After the reaction mixture has been stored overnight, it is warmed to 50° C. for 4 hours, ice-water is added and the precipitate formed is filtered off. For purification, the solid is partitioned between methylene chloride and 2N NaOH, the organic phase is dried over Na₂SO₄ and evaporated and the residue is crystallised from methylene chloride/diisopropyl ether. Yield: 7.8 g (40% of theory), melting point 222°–223° C.; N calculated 13.58%; N found 13.48%

9. 10-(3-Aminophenyl)-2,3-dihydroimidazo-[2,1-b]-quinoazolin-5(10H)-one

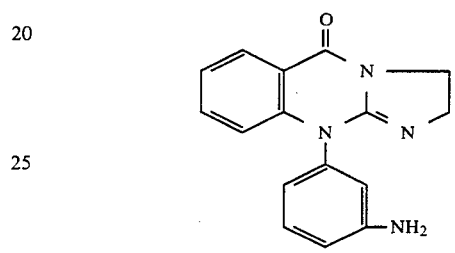

20 ml (0.413 mol) of 100% pure hydrazine hydrate are added to a suspension of 9.9 g (32 mmols) of 10-(3-nitrophenyl)-2,3-dihydroimidazo-[2,1-b]-quinazolin-5(10H)-one and 2 g of Pd-on-charcoal (10% strength) in 500 ml of methanol and the mixture is boiled under reflux for 6 hours.

After addition of in each case the same amount of catalyst and hydrazine hydrate, the mixture is boiled again for 6 hours and is filtered hot, the filtrate is evaporated and the residue is extracted by stirring with water. Yield: 3 g (34% of theory), melting point 309°–311° C.; N calculated 20.13%; N found 20.13%.

10. 10-(4-Methylsulphinylphenyl)-2,3-dihydroimidazo-[2,1-b]-quinazolin-5(10H)-one monohydrate

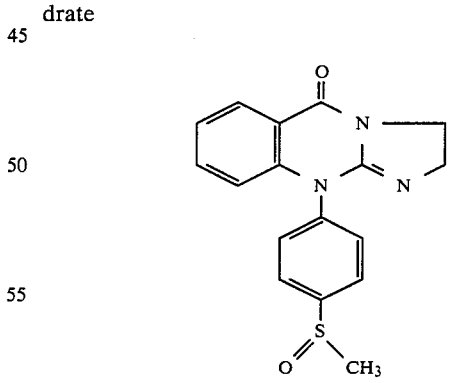

After addition of 0.77 ml of 30% strength hydrogen peroxide, a solution of 2.04 g (6.6 mmols) of 10-(4-methylthiophenyl)-2,3-dihydroimidazo-[2,1-b]-quinazolin-5(10H)-one in 20 ml of glacial acetic acid is first stored for 22 hours, and, after addition of another 0.2 ml of 30% strength hydrogen peroxide, is stored for another 7 hours at room temperature. Excess peroxide is destroyed by addition of a spatula-tip of platinum black, the mixture is filtered and the filtrate is evaporated. The residue is taken up in water, and saturated KHCO₃ solution is added to the solution. The precipitate formed is filtered off and is chromatographed on aluminium oxide 90 (Merck), first with ethyl acetate and then with methylene chloride/methanol (95:5). The fractions containing the product are evaporated and the resulting residue is crystallised from methylene chloride/diisopropyl ether. Yield: 1.6 g (71% of theory), melting point 257°–260° C., N calculated 12.24%; N found 12.01% 11.

10-(3-Trifluoromethyl)-imidazo-[2,1-b]-quinazolin-5(10H)-one

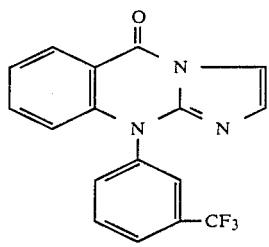

7 g of active manganese dioxide are added to a solution of 1.65 g (5 mmols) of 10-(3-trifluoromethyl)-2,3-dihydroimidazo-[2,1-b]-quinazolin-5(10H)-one in 30 ml of absolute methylene chloride, and the mixture is stored overnight at room temperature and boiled under reflux for 90 minutes. The mixture is filtered, the filtrate is evaporated and the residue is chromatographed with ethyl acetate on silica gel. Yield: 0.5 g (30% of theory) and 0.95 g of mixed fractions, melting point 206°–208° C.; N calculated 12.78%; N found 12.69%.

We claim:

1. A quinazolinone derivative of the formula

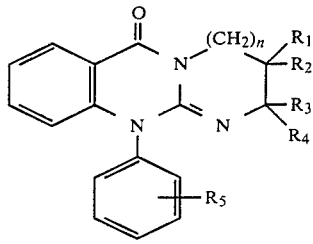

wherein
$R_1$, $R_2$, $R_3$ and $R_4$ each represent hydrogen and n represents 0 or 1, or
$R_1$ and $R_3$ represent hydrogen,
$R_2$ and $R_4$ together represent a bond and n represents 0, or
$R_1$ and $R_3$ together represent a bond,
$R_2$ and $R_4$ together represent the grouping

and n represents 0, and
$R_5$ represents a trifluoromethyl, methylthio, methylsulphonyl, nitro or amino group.

2. A compound of claim 1 which is 10-(3-nitrophenyl)-2,3-dihydroimidazo-[2,1-b]-quinazolin-5(10H)-one.

3. A compound of claim 1 which is 10-(3-trifluoromethylphenyl)-2,3-dihydroimidazo-[2,1-b]-quinazolin-5(10H)-one.

4. A compound of claim 1 which is 11-(3-nitrophenyl)-2,3,4,6-terrahydropyrimido[2,1-b]-quinazolin-6-one.

5. A compound of claim 1 which is 10-(3-aminophenyl)-2,3-dihydroimidazo-[2,1-b]-quinazolin-5(10H)-one.

* * * * *